(12) United States Patent
Zhang et al.

(10) Patent No.: US 11,439,845 B2
(45) Date of Patent: Sep. 13, 2022

(54) MULTI-LEAF COLLIMATOR

(71) Applicant: SHANGHAI UNITED IMAGING HEALTHCARE CO., LTD., Shanghai (CN)

(72) Inventors: Jian Zhang, Shanghai (CN); Kun Yang, Shanghai (CN); Xiao Fang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 422 days.

(21) Appl. No.: 16/417,750

(22) Filed: May 21, 2019

(65) Prior Publication Data
US 2020/0023198 A1    Jan. 23, 2020

(30) Foreign Application Priority Data
Jul. 23, 2018    (CN) .......................... 201810813687.9

(51) Int. Cl.
*A61N 5/10* (2006.01)
(52) U.S. Cl.
CPC .......... *A61N 5/1045* (2013.01); *A61N 5/1036* (2013.01); *A61N 2005/1074* (2013.01)
(58) Field of Classification Search
CPC .......... A61N 2005/1074; A61N 5/1045; A61N 5/1036; A61N 5/1065
See application file for complete search history.

(56) References Cited

U.S. PATENT DOCUMENTS

| | | |
|---|---|---|
| 8,384,049 B1 | 2/2013 | Broad |
| 2002/0101959 A1 | 8/2002 | Kato et al. |
| 2005/0063516 A1 | 3/2005 | Kato et al. |
| 2007/0164239 A1 | 7/2007 | Terwilliger et al. |
| 2008/0292058 A1 | 11/2008 | Nagata |
| 2009/0262901 A1 | 10/2009 | Broad et al. |

(Continued)

FOREIGN PATENT DOCUMENTS

| | | |
|---|---|---|
| CN | 201226257 Y | 4/2009 |
| CN | 104667427 A | 6/2015 |

(Continued)

OTHER PUBLICATIONS

First Office Action in Chinese Application No. 201810813687.9 dated Feb. 6, 2020, 14 pages.

(Continued)

*Primary Examiner* — Christine H Matthews
*Assistant Examiner* — Joshua Daryl D Lannu
(74) *Attorney, Agent, or Firm* — Metis IP LLC

(57) ABSTRACT

The present disclosure relates a multi-leaf collimator. The multi-leaf collimator may include a plurality of leaf modules. Each leaf module of the plurality of leaf modules may include a leaf configured to shield a portion of beams emitted by a radiation source. The leaf may be movable along a guide rail of the multi-leaf collimator. Each leaf module may also include a drive mechanism including a first drive component and a second drive component. The first drive component and the second drive component may be both connected to the leaf. The first drive component and the second drive component may jointly actuate the leaf to move along the guide rail.

21 Claims, 11 Drawing Sheets

(56) References Cited

U.S. PATENT DOCUMENTS

| | | |
|---|---|---|
| 2010/0278310 A1 | 11/2010 | Dehler et al. |
| 2012/0043482 A1 | 2/2012 | Prince et al. |
| 2012/0203490 A1* | 8/2012 | Sayeh ............... A61N 5/1075 |
| | | 702/105 |
| 2014/0217312 A1 | 8/2014 | Echner et al. |
| 2014/0239204 A1 | 8/2014 | Orton et al. |
| 2015/0170778 A1 | 6/2015 | Echner et al. |
| 2016/0106387 A1 | 4/2016 | Kahn et al. |
| 2016/0361566 A1 | 12/2016 | Larkin et al. |
| 2017/0084359 A1 | 3/2017 | Constantin et al. |
| 2017/0143995 A1 | 5/2017 | Bergfjord |
| 2017/0281972 A1 | 10/2017 | Zhang et al. |
| 2018/0193671 A1 | 7/2018 | Chappelow et al. |

FOREIGN PATENT DOCUMENTS

| | | |
|---|---|---|
| CN | 204972723 U | 1/2016 |
| CN | 204972724 U | 1/2016 |
| CN | 107929955 A | 4/2018 |
| EP | 2524718 A1 | 11/2012 |
| JP | 2004089214 A | 3/2004 |
| JP | 2017205215 A | 11/2017 |

OTHER PUBLICATIONS

First Office Action in Chinese Application No. 201911220461.9 dated Feb. 3, 2021, 22 pages.

* cited by examiner

MULTI-LEAF COLLIMATOR

CROSS-REFERENCE TO RELATED APPLICATIONS

This application claims priority to Chinese Patent Application No. 201810813687.9, filed on Jul. 23, 2018, the contents of which are hereby incorporated by reference in its entirety.

TECHNICAL FIELD

The present disclosure generally relates to radiotherapy, and more specifically relates to a multi-leaf collimator (MLC) and systems for actuating one or more leaves of the MLC.

BACKGROUND

Radiotherapy has been widely employed in cancer therapy by directing ionizing radiation towards a tumor. Multi-leaf collimator (MLC) is commonly used in radiotherapy to implement the precise delivery of radiation to the tumor. MLC may be mounted on a radiation delivery device (e.g., a radiation source of the radiation delivery device). By moving one or more leaves of the MLC, various radiation fields may be formed, which may conform the shape(s) of the tumor. The moving speed of the leaves may affect the overall treatment time. The faster the moving speed of the leaves are, the shorter the treatment time is. In general, the leaves of the MLC may be made of radiation-impermeable materials (e.g., tungsten), which may need relatively large driving force to reach a fast moving speed when actuated by a motor drive component. However, the large driving force will require a large size motor drive component, which may be difficult to implement due to the limited inner space of the radiation delivery device. Thus, it is desirable to improve the actuation way of the MLC to achieve large drive force without using the large size motor drive component.

SUMMARY

In one aspect of the present disclosure, a multi-leaf collimator is provided. The multi-leaf collimator may include a plurality of leaf modules. Each leaf module of the plurality of leaf modules may include a leaf and a drive mechanism. The leaf may be configured to shield a portion of beams emitted by a radiation source. The leaf may be movable along a guide rail of the multi-leaf collimator. The drive mechanism may include a first drive component and a second drive component. The first drive component and the second drive component may both be connected to the leaf. The first drive component and the second drive component may jointly actuate the leaf to move along the guide rail.

In some embodiments, the second drive component may include an air cylinder, a piston, and a first position encoder. The air cylinder may be configured to accommodate compressed gas. The piston may be connected to the air cylinder, and may be configured to output a driving force to the leaf when driven by the compressed gas. The first position encoder may be connected to the piston, and may be capable of moving with the piston to detect a position of the leaf.

In some embodiments, the multi-leaf collimator may further include a transmission shaft configured to transmit the driving force to the leaf. A first end of the transmission shaft may be connected to the piston, and a second end of the transmission shaft may be connected to the leaf.

In some embodiments, the transmission shaft may be flexible and may be configured to arrange the air cylinder flexibly. The leaf module may further include a shaft sleeve configured to accommodate the flexible transmission shaft.

In some embodiments, the first drive component may include a speed increaser configured to increase a revolution speed of the first drive component.

In some embodiments, the multi-leaf collimator may further include a transmission component coupled to the first drive component. The transmission component may be configured to transmit the driving force to the leaf.

In some embodiments, the transmission component may include a lead screw connected to the first drive component and rotatable with a rotation of a motor of the first drive component, and a nut fixed to the leaf. The lead screw may further include a plurality of external threads. The nut may further include a plurality of internal threads. The plurality of internal threads of the nut may be engageable with the external threads of the lead screw for actuating the leaf to move when the lead screw rotates.

In some embodiments, the first drive component and the second drive component may simultaneously actuate the leaf to move along the guide rail. The first drive component and the second drive component may actuate the leaf to move with a same speed.

In some embodiments, the first drive component and the second drive component may non-simultaneously actuate the leaf to move along the guide rail.

In some embodiments, the second drive component may firstly actuate the leaf to move to a first position at a first speed. The first drive component may actuate the leaf to move from the first position to a target position at a second speed. The second speed may be lower than the first speed.

In some embodiments, the multi-leaf collimator may further include a transmission component including a modified lead screw and a modified nut. The modified lead screw may be connected to the first drive component, and the modified nut may be fixed to the leaf.

In some embodiments, at least a portion of an outer circumference of the modified lead screw may include external threads.

In some embodiments, the modified lead screw may include a first surface and a second surface. A portion of the modified nut may include a gap. A thickness of the modified lead screw between the first surface and the second surface may be less than a width of the gap of the portion of the modified unit.

In some embodiments, the modified lead screw may not be engageable with the modified nut when the second drive component actuates the leaf to move. The modified lead screw may be engageable with the modified nut when the first drive component actuates the leaf to move.

In another aspect of the present disclosure, a system for controlling a multi-leaf collimator is provided. The system may include at least one storage device and at least one processor in communication with the at least one storage device. The at least one storage device may include a set of instructions for controlling a movement of the multi-leaf collimator. When executing the set of instructions, the at least one processor may be configured to cause the system to determine a target position that a leaf of the multi-leaf collimator needs to reach. The at least one processor may be configured to cause the system to actuate the leaf to move to the target position by a drive mechanism. The drive mechanism may include a first drive component and a second drive component. The first drive component and the second drive component may be both connected to the leaf.

In some embodiments, to actuate the leaf to move to the target position, the at least one processor may be further configured to cause the system to actuate the leaf to move to the target position by the first drive component and the second drive component simultaneously.

In some embodiments, to actuate the leaf to move to the target position, the at least one processor may be further configured to cause the system to actuate the leaf to move to a first position at a first speed by the second drive component, and actuate the leaf to move from the first position to the target position at a second speed by the first drive component. The second speed may be lower than the first speed.

In some embodiments, the multi-leaf collimator may include a transmission component including a modified lead screw and a modified nut. The modified lead screw may be connected to the first drive component, and the modified nut may be fixed to the leaf.

In some embodiments, the at least one processor may be further configured to cause the system to determine whether the modified lead screw is engaging with the modified nut. In response to a determination that the modified lead screw is not engageable with the modified nut, the at least one processor may be further configured to cause the system to actuate the leaf to move to a first position by the second drive component, and actuate the leaf to move from the first position to the target position by the first drive component.

In some embodiments, the at least one processor may be further configured to cause the system to in response to a determination that the modified lead screw is engageable with the modified nut, adjust the modified lead screw such that the modified lead screw is not engageable with the modified nut; actuate the leaf to move to a first position by the second drive component; and actuate the leaf to move from the first position to the target position by the first drive component.

In yet another aspect of the present disclosure, a method is provided. The method may be implemented on a computing device having at least storage device and at least one processor. The method may include determining a target position that a leaf of the multi-leaf collimator needs to reach, and actuate the leaf to move to the target position by a drive mechanism. The drive mechanism may include a first drive component and a second drive component. The first drive component and the second drive component may be both connected to the leaf.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
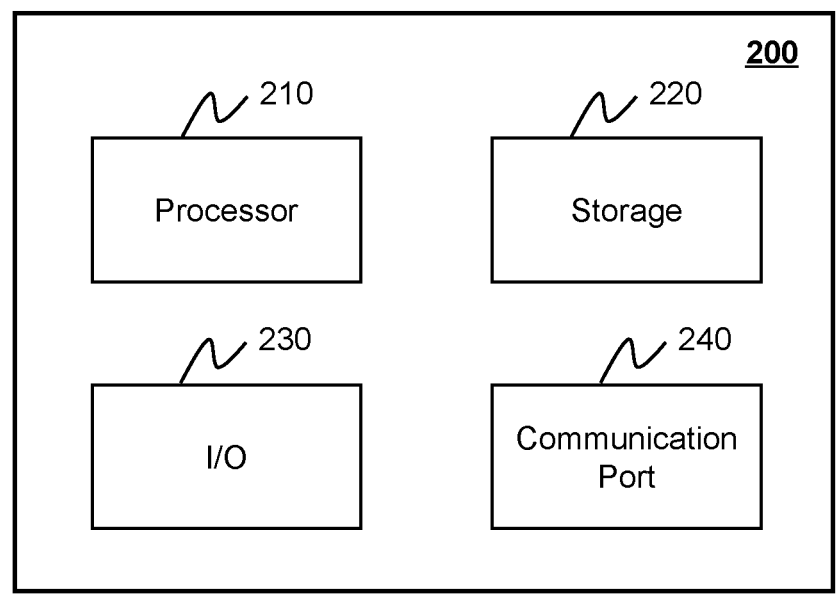
FIG. 2 is a schematic diagram illustrating exemplary hardware and/or software components of a computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to a multi-leaf collimator. The multi-leaf collimator may include a plurality of leaf modules. Each leaf module may include a leaf and a drive mechanism. The leaf may be configured to shield a portion of beams emitted by a radiation source. The drive mechanism may include a first drive component (e.g., a pneumatic component) and a second drive component (e.g., a motor drive component). The pneumatic component and the motor drive component may both be connected to the leaf. The pneumatic component and the motor drive component may jointly actuate the leaf to move along a guide rail. In some embodiments, the pneumatic component and the motor drive component may simultaneously actuate the leaf to move along the guide rail. Alternatively, the pneumatic component and the motor drive component may non-simultaneously actuate the leaf to move along the guide rail.

Figure 1:
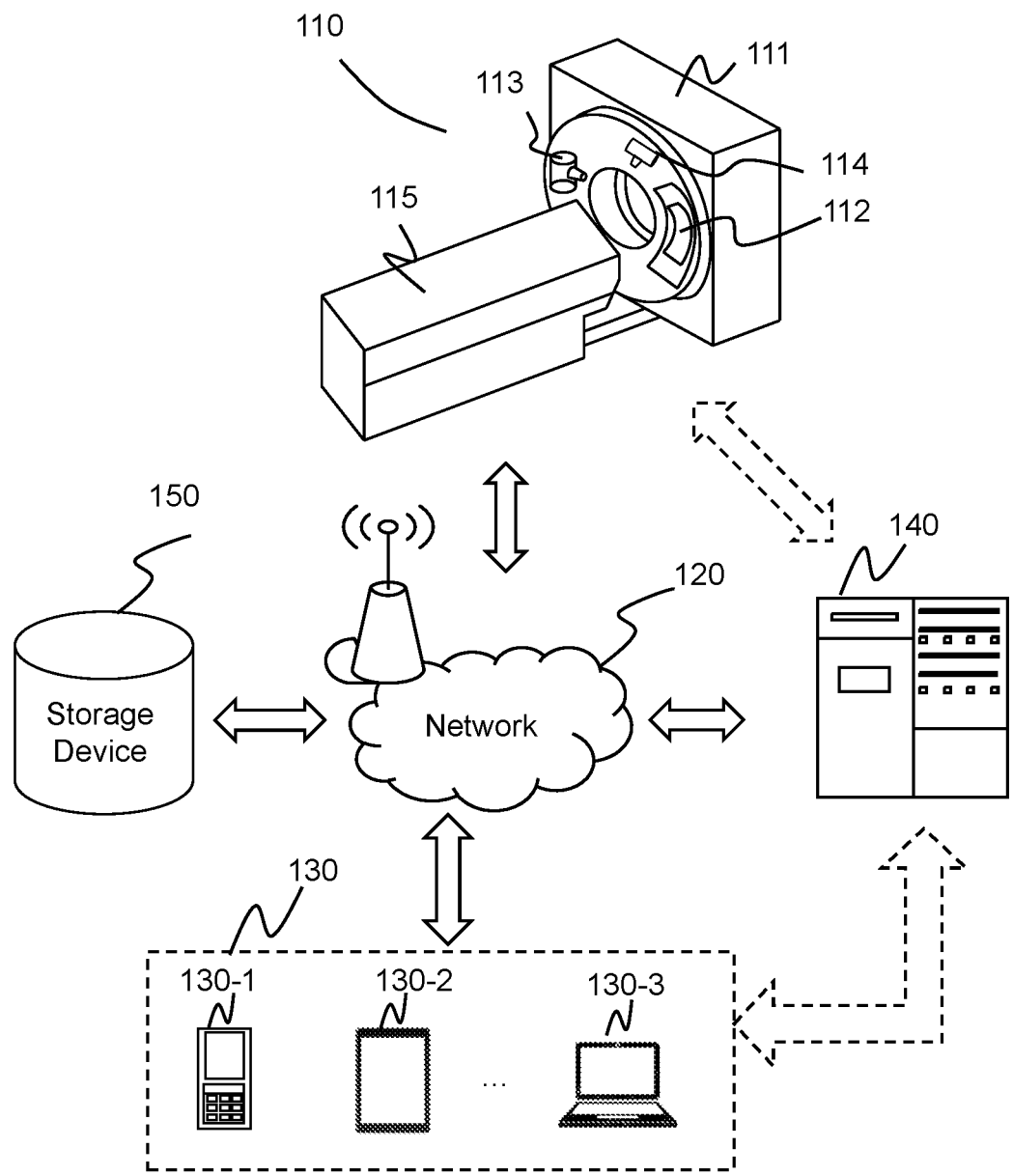
FIG. 1 is a schematic diagram illustrating an exemplary radiation system according to some embodiments of the present disclosure.

FIG. 1 is a schematic diagram illustrating an exemplary radiation system according to some embodiments of the present disclosure. The radiation system 100 may include a radiation delivery device 110, a network 120, one or more terminals 130, a processing device 140, and a storage device 150. The components of the radiation system 100 may be connected in various ways. Merely by way of example, the radiation delivery device 110 may be connected to the processing device 140 through the network 120. As another example, the radiation delivery device 110 may be connected to the processing device 140 directly as indicated by the bi-directional arrow in dotted lines linking the radiation delivery device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the radiation delivery device 110 may simultaneously perform imaging and treatment on an object. Merely by way of example, the radiation delivery device 110 may include an imaging assembly, a treatment radiation source (e.g., the first radiation source 114), a gantry 111, and a table 1150. The imaging assembly may include a conventional CT, a cone beam CT (CBCT), a helical CT, a multi-slice CT, a PET-CT, or the like, or any combination thereof. The imaging assembly may be configured to generate one or more images before, during or after radiotherapy. As shown in FIG. 1, the imaging assembly may include an imaging radiation source (e.g., the second radiation source 113) and a radiation detector 112 opposite to the second radiation source 113. The gantry 111 may include a rotary ring (not shown in FIG. 1). The rotary ring may be configured to accommodate the second radiation source 113, the radiation detector 112, and the first radiation source 114. In some embodiments, the first radiation source 114 may emit a first beam toward a first region (e.g., a tumor) of an object that is placed on the table 115. The second radiation source 113 may emit a second beam toward a second region (e.g., an imaging region) of the object. In some embodiments, the intensity of the first beam may be different from the intensity of the second beam. For example, the energy of the first beam may be several megavolts (MV), this energy being greater than that of the second beam, which may be several kilovolts (kV). The object may be a biological object (e.g., a patient, an animal) or a non-biological object. In the present disclosure, "object" and "subject" are used interchangeably. The radiation detector 112 may be configured to detect radiation emitted from the second radiation source 113. It should be noted that the above descriptions of the radiation delivery device 110 are merely provided for the purposes of illustration, and not intended to limit the scope of the present disclosure. In some embodiments, the imaging assembly in the radiation delivery device 110 may be omitted, and the radiation delivery device 110 may include only one radiation source (e.g., the first radiation source 114) for delivering radiation for radiotherapy or imaging.

In some embodiments, the radiation delivery device 110 may further include one or more MLCs (not shown in FIG. 1). The MLC(s) may be configured to collimate the radiation beam(s) of the radiation delivery device 110 and/or define the beam shape(s) thereof to form one or more radiation fields. An MLC may include multiple leaves. In some embodiments, the first radiation source 114 may include or be associated with an MLC. More descriptions of the MLC may be found elsewhere in the present disclosure (e.g., FIG. 4 and the descriptions thereof).

The network 120 may facilitate exchange of information and/or data. In some embodiments, one or more components of the radiation system 100 (e.g., the radiation delivery device 110, the terminal 130, the processing device 140, or the storage device 150) may send information and/or data to another component(s) in the radiation system 100 via the network 120. For example, the processing device 140 may cause, via the network 120, the first radiation source 114 of the radiation delivery device 110 to emit radiation beams. As another example, the processing device 140 may obtain, via the network 120, user instruction(s) for actuating a leaf to move to a target position from the terminal 130. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the radiation delivery device 110. In some embodiments, the terminal 130 may operate the radiation delivery device 110 via a wireless connection. In some embodiments, the terminal 130 may receive information and/or instructions inputted by a user, and send the received information and/or instructions to the radiation delivery device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the radiation delivery device 110, the terminal 130, or the storage device 150. For example, the processing device 140 may determine a target position of a leaf of an MLC. As another example, the processing device 140 may control a drive mechanism to actuate the leaf of to move to the target position. The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the terminal 130, the processing device 140). One or more components of the radiation system 100 may access the data or instructions stored in the storage device 150 via the network 120. In some embodiments, the storage device 150 may be directly connected to or communicate with one or more components of the radiation system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the radiation delivery device 110, the terminal 130, the storage device 150, and/or any other component of the radiation system 100. For example, the processor 210 may determine a target position that a leaf of a MLC needs to reach. As another example, the processor 210 may control a pneumatic component and/or a motor drive component to actuate the leaf to move to the target position. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
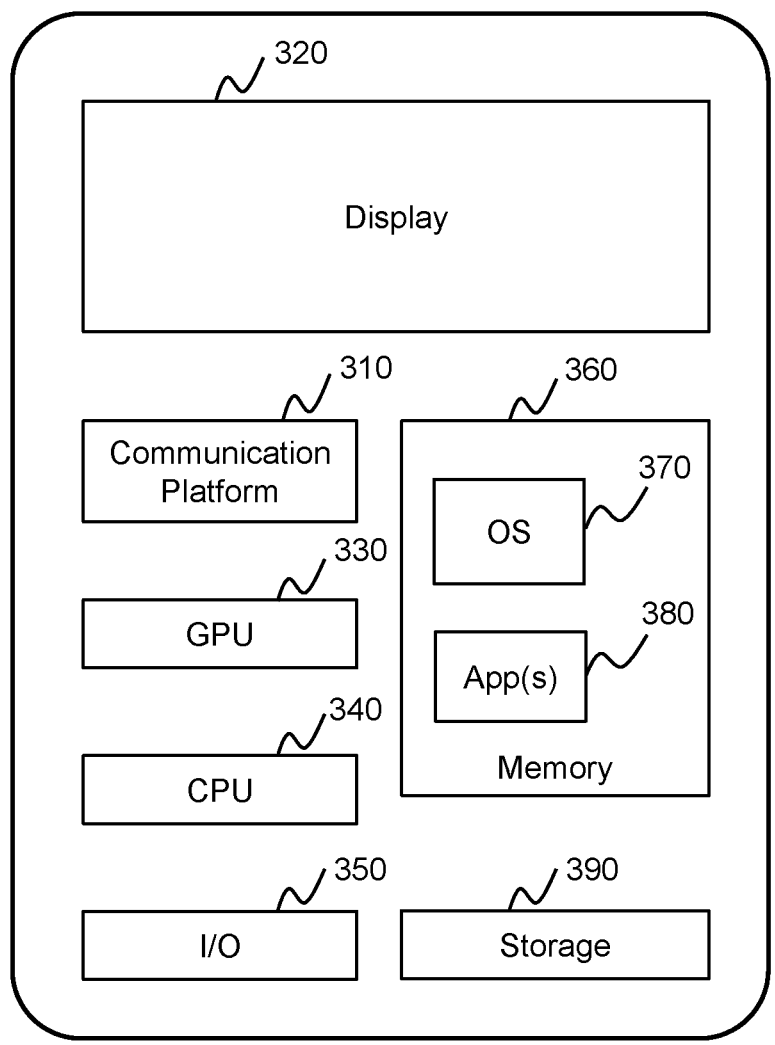
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to actuate the movement a multi-leaf collimator as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
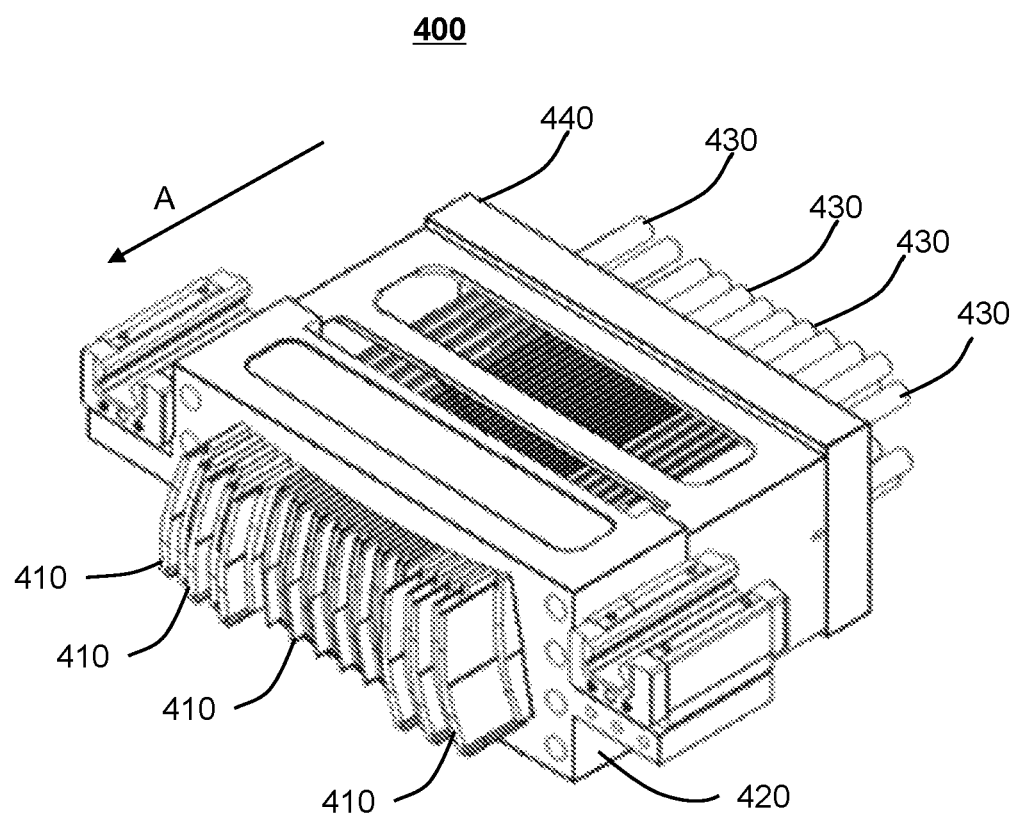
FIG. 4 is a schematic diagram illustrating an exemplary MLC according to some embodiments of the present disclosure.

FIG. 4 is a schematic diagram illustrating an exemplary MLC according to some embodiments of the present disclosure. As shown in FIG. 4, the MLC 400 may include a plurality of leaf modules, a housing 420, and a motor base 440. In some embodiments, the housing 420 may be configured to accommodate the plurality of leaf modules. In some embodiments, the plurality of leaf modules may include a plurality of leaves 410 and a plurality of drive mechanisms 430. The plurality of leaves 410 may be configured to shield a portion of beams emitted by a radiation source (e.g., the first radiation source 114). The plurality of drive mechanisms 430 may be supported and/or accommodated by the motor base 440. The MLC 400 may further include a guide rail box including a plurality of guide rails. Each guide rail of the plurality of guide rails may be configured to guide a movement of a leaf of the plurality of leaves 410. That is, a leaf 410 may be movable along a guide rail of the plurality of guide rails disposed on the guide rail box.

In some embodiments, the MLC 400 may include 64 leaves. However, it shall be understood that the number of the leaves in the MLC 400 may vary. For example, the number of the leaves in the MLC 400 may be 12, 24, 32, 48, 80, 100, 128, etc. In some embodiments, to shield beams emitted by the radiation source (e.g., the first radiation source 114), the plurality of leaves 410 may be made of radiation-impermeable materials (e.g., tungsten). However, in order to reduce the weight of the leaves, only a portion of the leaves 410 that shield the beams may have a high-Z material, while the remaining portion of the leaves 410 may include lighter-weight materials. For example, a portion of a leaf 410 may be made of a radiation-impermeable material (e.g., tungsten), while the remaining portion of the leaf 410 may be made of one or more other materials (e.g., a material that is less dense or lighter than the radiation impermeable material, such as stainless steel or titanium).

In some embodiments, at least some of the plurality of leaves 410 may be configured to move simultaneously. By simultaneously moving at least some of the plurality of leaves 410, an aperture (also referred to as radiation field) may be formed. A portion of beams emitted from the radiation source (e.g., the first radiation source 114) may pass through the aperture, and further be delivered to a treatment region (e.g., a tumor). The other portion of beams may be blocked by the leaves 410 of the MLC 400. In some embodiments, the plurality of drive mechanisms 430 may facilitate the movement of the plurality of leaves 410 such that the MLC 400 can transition the leaves 410 between a first aperture shape and a second aperture shape. For example, a leaf 410 may be capable of transitioning from a first position to a second position (e.g., from a closed position to a target position). In some embodiments, each leaf 410 may be actuated to move independently, e.g., by its corresponding drive mechanism 430.

In some embodiments, each of one or more leaves of the MLC 400 may rapidly transition from a first position to a second position so that the overall treatment time can be reduced. In some embodiments, the drive mechanism 430 may include one or more drive components, such as a motor drive component, a pneumatic component, a loaded spring, or the like. In some embodiments, each of one or more leaves 410 of the MLC 400 may be actuated and/or driven by at least two drive components so as to increase the moving speed of the each leaf 410, thereby rapidly forming an aperture (or a radiation filed). In some embodiments, when a leaf is actuated by one drive component, the driving power of actuating the leaf may be determined according to Equation (1) as below:

$$P=\vec{F}\cdot\vec{v}, \quad (1)$$

where P refers to the driving power of actuating the leaf; $\vec{F}$ refers to the driving force of actuating the leaf; and $\vec{v}$ refers to the moving speed of the leaf.

As is known, the driving force $\vec{F}$ may depend on characteristic of the leaf (e.g., the weight of the leaf, the size of the leaf, or the like). According to Equation (1), when the driving force $\vec{F}$ remains constant, in order to increase the moving speed $\vec{v}$ of the leaf, the driving power P may need to be improved. In some embodiments, if the drive component is a motor drive component, the motor drive component may need to have a large size to provide high driving power P. However, the inner space of the radiation delivery device 110 is too limited to accommodate a plurality of large size motor drive components. Thus, to solve this problem, a second drive component may be introduced. Merely by way of example, a leaf may be actuated by two drive components to increase the moving speed of the leaf. The driving power of actuating the leaf may be determined according to Equation (2) as below:

$$P=\vec{F}\cdot\vec{v}=(\vec{F_1}+\vec{F_2})\cdot\vec{v}=P_1+P_2, \quad (2)$$

where $\vec{F_1}$ refers to the first driving force corresponding to a first drive component; $\vec{F_2}$ refers to the second driving force corresponding to a second drive component; $P_1$ refers to the first driving power corresponding to the first drive component; $P_2$ refers to the second driving power corresponding to the second drive component.

Figure 5:
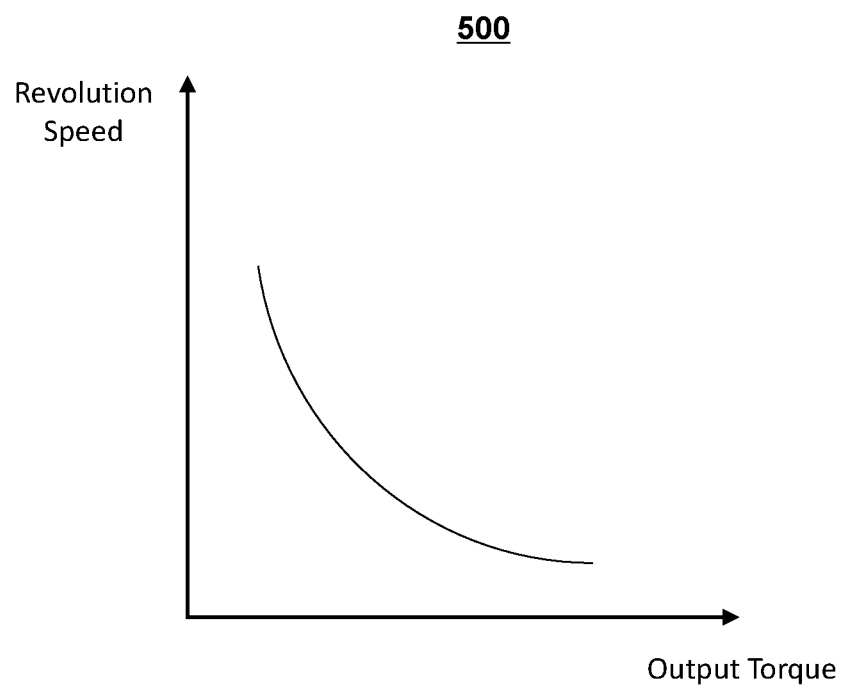
FIG. 5 is a schematic diagram illustrating an exemplary relationship between an output torque and a revolution speed according to some embodiments of the present disclosure.

In some embodiments, the second drive component may be different from the first drive component. In some embodiments, the first drive component may be a motor drive component, and the second drive component may be a pneumatic component. The second drive component (e.g., the pneumatic component) may provide a larger driving force for the leaf than the first drive component (e.g., the motor drive component). Accordingly, the second drive component (e.g., the pneumatic component) may provide a larger driving power than the first drive component (e.g., the motor drive component). In some embodiments, the pneumatic component may implement the quick movement of the leaf, and the motor drive component may implement the precise movement of the leaf. In some embodiments, the driving power of the pneumatic component may be provided by compressed gas. The driving power of the motor drive component may depend on an output torque and a revolution speed. FIG. 5 is a schematic diagram illustrating an exemplary relationship between an output torque and a revolution speed according to some embodiments of the present disclosure. As shown in FIG. 5, for a motor drive component with a constant driving power, the smaller the output torque is, the higher the revolution speed is. In some embodiments, the revolution speed may be increased by reducing the output torque, which may increase the moving speed of the leaf. In some embodiments, the motor drive component may include a speed increaser configured to increase the revolution speed. More descriptions of the drive mechanism (e.g., the pneumatic component, the motor drive component) may be found elsewhere in the present disclosure (e.g., FIGS. 6A and 6B, and the descriptions thereof).

It should be noted that the above descriptions of the MLC 400 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, a drive mechanism 430 may simultaneously actuate two or more leaves to move. In some embodiments, one of the leaves may be actuated by only one drive component. Alternatively or additionally, one of the leaves may be actuated by three or more drive components. For example, a leaf may be actuated by three drive components, such as a motor drive component, a pneumatic component, and a loaded spring.

Figure 6A:
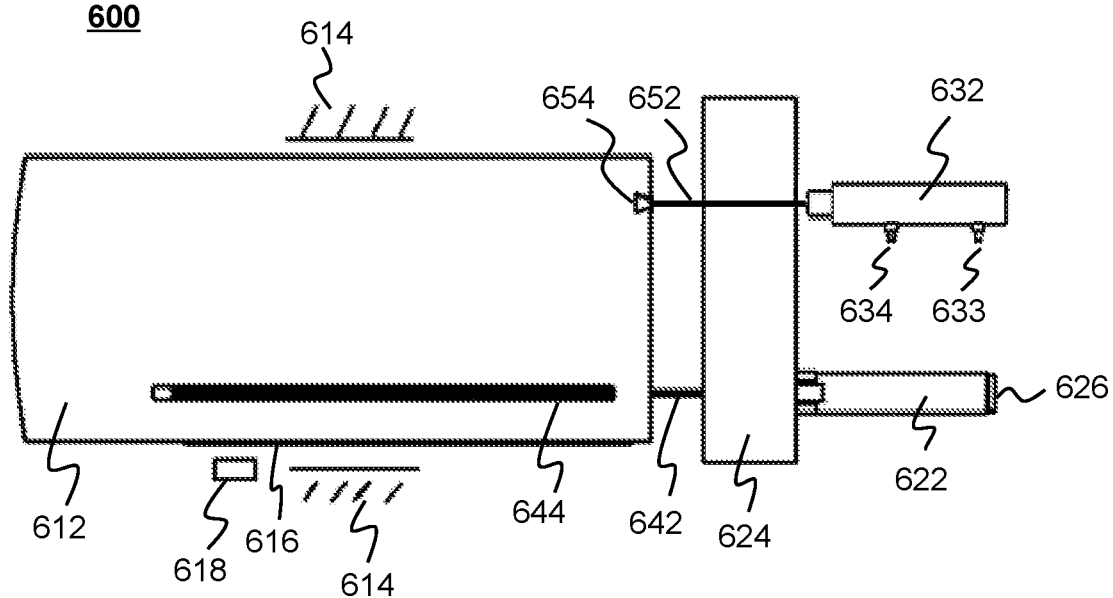
FIGS. 6A and 6B are schematic diagrams illustrating two exemplary leaf modules 600 and 605 according to some embodiments of the present disclosure.
Figure 6B:
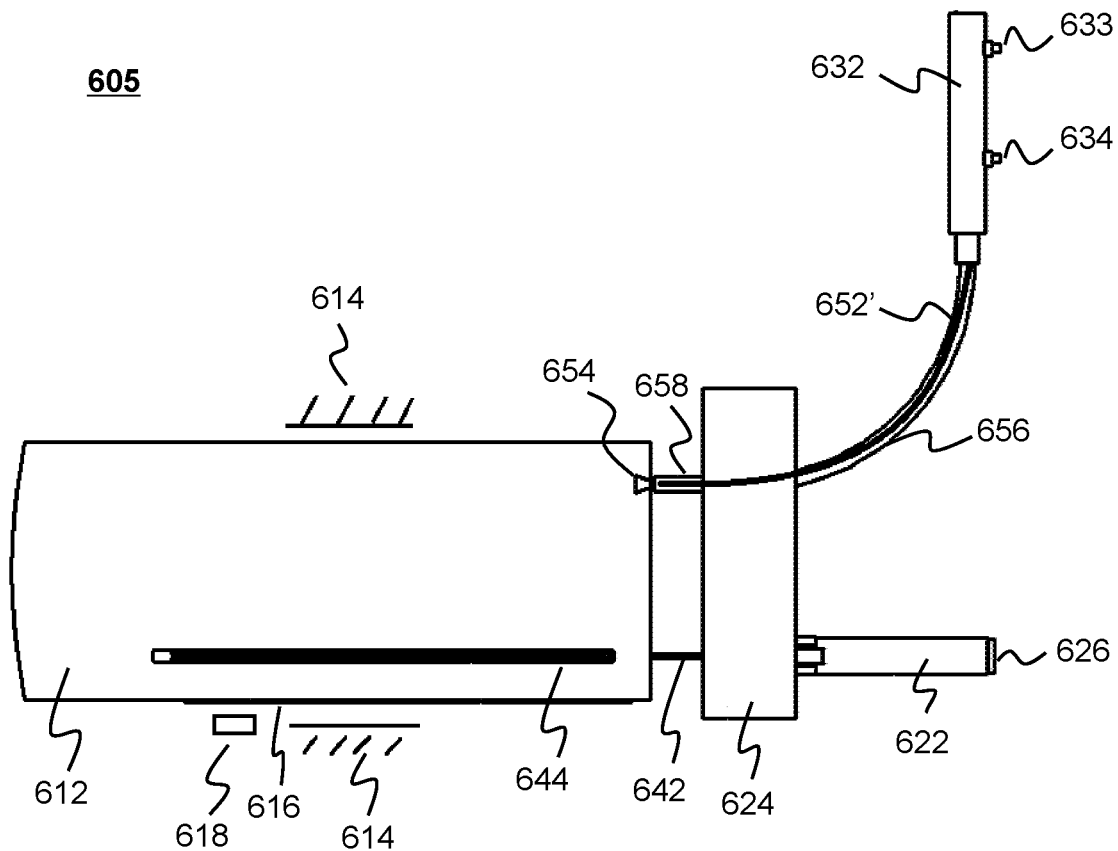

FIGS. 6A and 6B are schematic diagrams illustrating two exemplary leaf modules 600 and 605 according to some embodiments of the present disclosure. At least some of the leaves in an MLC (e.g., the MLC 400 as illustrated in FIG. 4) may be configured as the leaf module 600 as illustrated in FIG. 6A or the leaf module 605 as illustrated in FIG. 6B. Unless otherwise stated, like reference numerals in the leaf module 600 and the leaf module 605 refer to like components having the same or similar functions. Herein, taking the leaf module 600 as an example to illustrate the structure of one or more leaves in the MLC (e.g., the MLC 400).

The leaf module 600 may be disposed in a housing (e.g., the housing 420) that can accommodate a plurality of leaf modules. As shown in FIG. 6A, the leaf module 600 may include a leaf 612 and a guide rail 614. The leaf 612 may be configured to shield a portion of beams emitted by a radiation source (e.g., the first radiation source 114). The guide rail 614 may be disposed on two sides of the leaf 612. The leaf 612 may be movable along the guide rail 614. For example, the leaf 612 may move from left or right as indicated in FIG. 6A along the guide rail 614.

In some embodiments, the leaf module 600 may include a position detection component configured to detect a position of the leaf 612. As shown in FIG. 6A, the position detection component may include a magnetic grid 616 and a magnetic head 618 configured to cooperatively detect the position of the leaf 612. The magnetic grid 616 may be mounted on the leaf 612, and the magnetic head 618 may be disposed with respect to the magnetic grid 616. In some embodiments, when the leaf 612 moves, the magnetic grid 616 may move accompanying the leaf 612 while the magnetic head 618 may keep static. Thus, relative movement between the magnetic grid 616 and the magnetic head 618 may be produced. The magnetic field of the magnetic grid 616 in the magnetic head 618 may change due to the relative movement, and further the magnetic head 618 can detect the change of the magnetic field. The magnetic head 618 may convert the detected change of the magnetic field to position information of the leaf 612 and output the position information of the leaf 612. Alternatively or additionally, the magnetic head 618 may be mounted on the leaf 612, and the magnetic grid 616 may be disposed with respect to the magnetic head 618. In some embodiments, when the leaf 612 moves, the magnetic head 618 may move accompanying the leaf 612 while the magnetic grid 616 may keep static. Thus, relative movement between the magnetic head 618 and the magnetic grid 616 may be produced. The magnetic field of the magnetic grid 616 in the magnetic head 618 may change due to the relative movement, and further the magnetic head 618 can detect the change of the magnetic field. The magnetic head 618 may convert the detected change of the magnetic field to position information of the leaf 612 and output the position information of the leaf 612. In some embodiments, the magnetic head 618 may include a magnetic sensor configured to detect the change of the magnetic field of the magnetic grid 616. In some embodiments, the magnetic sensor may be a Hall sensor. The magnetic grid 616 may be a bar magnet (e.g., a multi-pole bar magnet). When the bar magnet moves relative to the Hall sensor, the magnetic field in the Hall sensor may change, and the Hall sensor may detect the change of the magnetic field. The Hall sensor may output pulse(s) based on the detected change of the magnetic field. In some embodiments, a certain amount of the change of the magnetic field may correspond to one pulse. Besides, the change of the magnetic field may have a relationship with the displacement of the bar magnet. Thus, according to the pulse(s) outputted by the Hall sensor, the displacement of the leaf 612 may be determined. The current position of the leaf 612 may be determined based on the displacement of the leaf 612 and an original position of the leaf 612. It should be noted that the magnetic sensor is not limited to the Hall sensor, and may be other magnetic sensor(s) that can detect the change of the magnetic field.

As shown in FIG. 6A, the leaf module 600 may include a drive mechanism. The drive mechanism may include two drive components, such as a first drive component (e.g., a motor drive component 620) and a second drive component (e.g., a pneumatic component 630). The motor drive component 620 and the pneumatic component 630 may be both connected to the leaf 612. The motor drive component 620 and the pneumatic component 630 may jointly actuate the leaf 612 to move along the guide rail 614.

In some embodiments, the motor drive component 620 may include a motor 622, a motor base 624, and a second position encoder 626. The motor 622 may be configured to generate a driving force to actuate the leaf 612 to move. The motor base 624 may be configured to support the motor 622. The second position encoder 626 may be connected to the motor and configured to detect the displacement of the leaf 612. In some embodiments, the second position encoder 626 may be located at one end of the motor 622 (e.g., one end that away from the leaf 612). When the motor 622 rotates, the second position encoder 626 may measure a rotation angle or revolutions of the motor 622. According to the rotation angle or the revolutions of the motor 622, the displacement of the leaf 612 may be determined. Then the current position of the leaf 612 may be determined based on the displacement of the leaf 612 and an original position of the leaf 612. In some embodiments, the second position encoder 626 may be an incremental encoder. Alternatively, the second position encoder 626 may be an absolute encoder. In some embodiments, the motor drive component 620 may further include a speed increaser (e.g., a gear box) configured to increase a revolution speed of the motor 622. In some embodiments, the speed increaser may include at least one pair of gears (e.g., a larger gear and a smaller gear). The low revolution speed of the larger gear may be converted to the high revolution speed of the smaller gear. The high revolution speed may be used as an output of the motor 622, thus improving the moving speed of the leaf 612.

In some embodiments, the leaf module 600 may include a transmission component 640 coupled to the motor drive component 620. The transmission component 640 may be configured to transmit the driving force to the leaf 612. In some embodiments, the transmission component 640 may include a lead screw 642 and a nut 644. The lead screw 642 may be connected to the motor drive component 620 (e.g., the motor 622) and rotatable with the rotation of the motor 622. The nut 644 may be fixed to the leaf 612. The lead screw 642 may include a plurality of external threads (not shown in FIG. 6A), and the nut 644 may include a plurality of internal threads (not shown in FIG. 6A). The internal thread(s) of the nut 644 may be engageable with the external thread(s) of the lead screw 642 for actuating the leaf 612 to move when the lead screw 642 rotates. In some embodiments, the nut 644 may be omitted, and the leaf 612 may include a plurality of internal threads (not shown in FIG. 6A). The internal thread(s) of the leaf 612 may be engageable with the external thread(s) of the lead screw 642 for actuating the leaf 612 to move when the lead screw 642 rotates. The rotation movement of the motor 622 may be converted to the linear movement of the leaf 612 via the transmission component 640 (e.g., via the engagement of the lead screw 642 and the nut 644).

The pneumatic component 630 may include an air cylinder 632. The air cylinder 632 may include an air inlet 633 and an air outlet 634. The air cylinder 632 may be configured to accommodate compressed gas. The pneumatic component 630 may also include a piston (not shown in FIG. 6A) connected to and/or within the air cylinder 632. The piston may be configured to output a driving force to the leaf 612 when driven by the compressed gas. For example, the piston may move in the air cylinder 632 to provide the driving force to the leaf 612. In some embodiments, the pneumatic component 630 may also include a first position encoder (not shown in FIG. 6A) connected to the piston. The first position encoder may be capable of moving with the piston to detect the position of the leaf 612. In some embodiments, the first position encoder may be an absolute encoder. More description of the pneumatic component 630 may be found elsewhere in the present disclosure (e.g., FIG. 7 and the descriptions thereof).

The leaf module 600 may also include a transmission shaft configured to transmit the driving force to the leaf 612. A first end of the transmission shaft may be connected to the piston of the pneumatic component 630. A second end of the transmission shaft may be connected to the leaf 612. When the piston of the pneumatic component 630 moves, the transmission shaft moves accordingly and transmit the driving force to the leaf 612, thereby actuating the leaf 612 to move along the guide rail 614.

In some embodiments, as shown in FIG. 6A, the transmission shaft may include a rigid transmission shaft 652. The rigid transmission shaft 652 may be made of a rigid material. In some embodiments, a first end (e.g., the right end as indicated in FIG. 6A) of the rigid transmission shaft 652 may be connected to the pneumatic component 630 (e.g., the piston of the pneumatic component 630), and a second end (e.g., the left end as indicated in FIG. 6A) of the rigid transmission shaft 652 may be connected to the leaf 612. The connection ways may include bolt connection, welding, riveting, interference fit, or the like, or any combination thereof. Merely by way of example, the second end of the rigid transmission shaft 652 (e.g., the end near the leaf 612) may be connected to a trapezoid block 654. The trapezoid block 654 may have a hole (e.g., a thread hole) through which the rigid transmission shaft 652 may be mounted and/or connected to the trapezoid block 654. The leaf 612 may include a dovetail slot (not shown in FIG. 6A) that matches with the trapezoid block 654. The trapezoid block 654 may be embedded in the dovetail slot to achieve the connection between the rigid transmission shaft 652 and the leaf 612. In some embodiments, the first end of the rigid transmission shaft 652 (e.g., the end near the pneumatic component 630) may be connected to the piston of the pneumatic component 630 in a similar or same manner. When the piston in the pneumatic component 630 moves linearly (e.g., move to left as indicated in FIG. 6A), the rigid transmission shaft 652 may move linearly (e.g., move to left as indicated in FIG. 6A) under the action of the piston. The rigid transmission shaft 652 may further actuate the leaf 612 to move linearly (e.g., move to left as indicated in FIG. 6A).

In some embodiments, each leaf module of an MLC (e.g., the MLC 400) may include a motor drive component and a pneumatic component. It should be noted that the inner space of the radiation delivery device 110 is too limited to accommodate, in parallel, a plurality of motor drive components and a plurality of pneumatic components corresponding to a plurality of leaves of the MLC. Besides, when an MLC (e.g., the MLC 40) is applied to a device in a magnetic field, such as a magnetic resonance radiation therapy (MR-RT), the pneumatic component 630 should be arranged away from the leaf 612 to reduce the interaction between a magnetic component (e.g., a piston made of a magnetic material) of the pneumatic component 630 and an MR magnet. Thus, different from the rigid transmission shaft 652 of the leaf module 600, the leaf module 605 in FIG. 6B may include a transmission shaft that is flexible.

As shown in FIG. 6B, the transmission shaft may include a flexible transmission shaft 652'. The flexible transmission shaft 652' may be configured to arrange the air cylinder 632 of the pneumatic component 630 flexibly, which may not need to arrange the pneumatic components and the motor drive components in parallel. In some embodiments, when the leaf module 605 is applied to MR-RT, the distance between the pneumatic component 630 and the leaf 612 may be increased due to the flexible transmission shaft 652'. For example, as shown in FIG. 6B, the pneumatic component 630 may be arranged away from the leaf 612 through the flexible transmission shaft 652', which may reduce the interaction between a magnetic component (e.g., a piston made of a magnetic material) of the pneumatic component 630 and an MR magnet. In some embodiments, the flexible transmission shaft 652' may be difficult to compress and stretch. For example, the flexible transmission shaft 652' may be a flexible pipe made of stainless steel, aluminum alloy, rubber, plastic, or the like, or any combination thereof.

The leaf module 605 may also include a shaft sleeve 656 and a guide sleeve 658. The shaft sleeve 656 may be configured to accommodate and/or protect the flexible transmission shaft 652'. In some embodiments, the shaft sleeve 656 may wrap up the whole flexible transmission shaft 652'. Alternatively, the length of the shaft sleeve 656 may be less than that of the flexible transmission shaft 652'. The shaft sleeve 656 may wrap up a first portion (e.g., a portion that is near the pneumatic component 630) of the flexible transmission shaft 652'. In some embodiments, the first portion of the flexible transmission shaft 652' near the pneumatic component 630 may be curved, and accordingly the corresponding portion of the shaft sleeve 656 may be curved. In some embodiments, the shaft sleeve 656 may be made of a flexible material, such as an extension spring.

The guide sleeve 658 may be configured to restrict a transmission path of the flexible transmission shaft 652'. For example, the guide sleeve 658 may be configured to guide a second portion (e.g., the portion near the leaf 612) of the flexible transmission shaft 652' to move along the guide sleeve 658. In some embodiments, the length of the guide sleeve 658 may be less than that of the flexible transmission shaft 652'. The guide sleeve 658 may be disposed to the second portion (e.g., the portion near the leaf 612) of the flexible transmission shaft 652'. In some embodiments, the guide sleeve 658 may include a guide cavity. The diameter of the guide cavity may be slightly greater than the outer diameter of the flexible transmission shaft 652' so that the flexible transmission shaft 652' may move in the guide cavity. When driven by the pneumatic component 630, the flexible transmission shaft 652' may move linearly after passing through the guide cavity of the guide sleeve 658. In some embodiments, the guide sleeve 658 may be made of a rigid material, such as metal, rigid plastic, or the like.

In some embodiments, a first end (e.g., the right end as indicated in FIG. 6B) of the flexible transmission shaft 652' may be connected to the pneumatic component 630 (e.g., the piston of the pneumatic component 630), and a second end (e.g., the left end as indicated in FIG. 6B) of the flexible transmission shaft 652' may be connected to the leaf 612. Similar to the rigid transmission shaft 652, the connection ways may include bolt connection, welding, riveting, interference fit, or the like, or any combination thereof. Merely by way of example, the second end of the flexible transmission shaft 652' (e.g., the end near the leaf 612) may be connected to a trapezoid block 654. The trapezoid block 654 may have a hole (e.g., a thread hole) through which the flexible transmission shaft 652' may be mounted and/or connected to the trapezoid block 654. The leaf 612 may include a dovetail slot (not shown in FIG. 6B) that matches with the trapezoid block 654. The trapezoid block 654 may be embedded in the dovetail slot to achieve the connection between the flexible transmission shaft 652' and the leaf 612. In some embodiments, the first end of the flexible transmission shaft 652' (e.g., the end near the pneumatic component 630) may be connected to the piston of the pneumatic component 630 in a similar or same manner.

In some embodiments, as shown in FIGS. 6A and 6B, the motor drive component 620 and the pneumatic component 630 may simultaneously actuate the leaf 612 to move along the guide rail 614. The motor drive component 620 and the pneumatic component 630 may actuate the leaf 612 to move with the same speed. In some embodiments, the pneumatic component 630 may provide a larger driving force for the leaf 612 than the motor drive component 620. Alternatively or additionally, the motor drive component 620 and the pneumatic component 630 may non-simultaneously actuate the leaf 612 to move along the guide rail 614. For example, the pneumatic component 630 may firstly actuate the leaf 612 to move to a first position at a first speed. The motor drive component 620 may actuate the leaf 612 to move from the first location to a target position at a second speed. The second speed may be lower than the first speed. In some embodiments, to implement the non-simultaneous actuation of the motor drive component 620 and the pneumatic component 630, the connection between the motor drive component 620 and the leaf 612 or the connection between the pneumatic component 630 and the leaf 612 should be changed or modified. That is, at least one of the transmission component 640 or the transmission shaft (e.g., the rigid transmission shaft 652, the flexible transmission shaft 652') should be modified or changed. Merely by way of example, the transmission component 640 may be modified. The modified transmission component may include a modified lead screw and a modified nut. The modified lead screw may be connected to the motor drive component 620, and the modified nut may be fixed to the leaf 612. Details regarding the modified transmission component may be found elsewhere in the present disclosure (e.g., FIG. 8 and the descriptions thereof).

It should be noted that the above descriptions of the leaf modules 600 and 605 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, for a leaf module of an MLC, the leaf module may include one or more motor drive components and/or one or more pneumatic components connected to the leaf of the leaf module.

In some embodiments, each leaf module of an MLC may include a motor drive component and a pneumatic component. That is, the MLC may include a plurality of motor drive components and a plurality of pneumatic components. In some embodiments, the plurality of motor drive components may be controlled by a motor controller. For example, the motor controller may include a plurality of motor control units, and each of which may control a motor drive component. As another example, a motor control unit may control two or more motor drive components. In some embodiments, the plurality of pneumatic components may be controlled by a pneumatic controller. For example, the pneumatic controller may include a plurality of pneumatic control units, and each of which may control a pneumatic component. As another example, a pneumatic control unit may control two or more pneumatic components.

Figure 7:
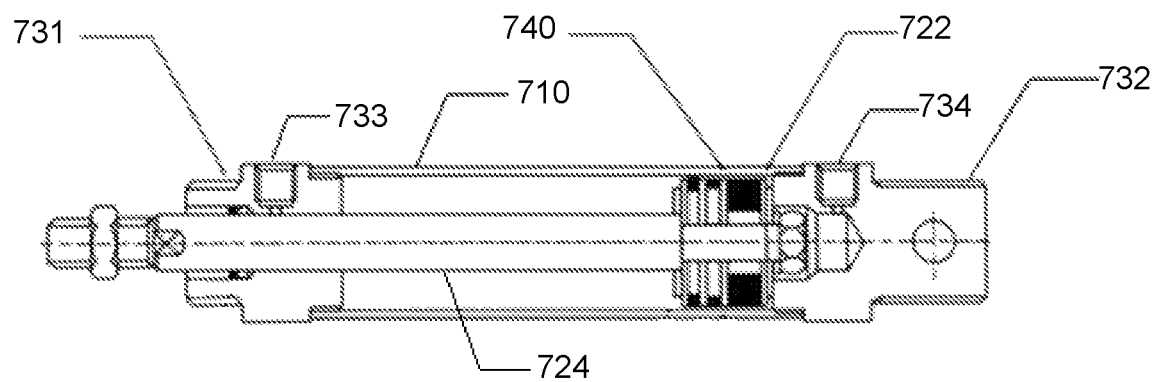
FIG. 7 is a schematic diagram illustrating an exemplary pneumatic component according to some embodiments of the present disclosure.

FIG. 7 is a schematic diagram illustrating an exemplary pneumatic component according to some embodiments of the present disclosure. The pneumatic component 700 may be an example of the pneumatic component 630 as illustrated in FIGS. 6A and 6B. As shown in FIG. 7, the pneumatic component 700 may include an air cylinder 710, a piston 722 within the air cylinder 710, and a piston rod 724 connected with the piston 722. The air cylinder 710 may be configured to accommodate compressed gas. The piston 722 and/or the piston rod 724 may move in the air cylinder 710 to provide a driving force to a leaf (e.g., the leaf 612) of an MLC. The pneumatic component 700 may also include a front end cap 731 and a rear end cap 732. The front end cap 731 and the rear end cap 732 may be fixed on two ends of the air cylinder 710. The front end cap 731 may include an air outlet 733, and the rear end cap 732 may include an air inlet 734. In some embodiments, the pneumatic component 700 may include a solenoid valve 740 configured to control the air outlet 733 and/or the air inlet 734.

In some embodiments, when the piston 722 and the piston rod 724 moves towards the front end cap 731 (e.g., move to left as indicated in FIG. 7), the solenoid valve 740 may open, and thus, a first portion of compressed gas may enter into the air cylinder 710 via the air inlet 734 and a second portion of compressed gas within the air cylinder 710 may be discharged via the air outlet 733. Alternatively, when the piston 722 and the piston rod 724 moves towards the rear end cap 732 (e.g., move to right as indicated in FIG. 7), the solenoid valve 740 may open, and thus, a third portion of compressed gas may enter into the air cylinder 710 via the air outlet 733 and a forth portion of compressed gas within the air cylinder 710 may be discharged via the air inlet 734. In this case, the air outlet 733 may be regarded as an air inlet, and the air inlet 734 may be regarded as an air outlet.

In some embodiments, a first end (e.g., the end away from the piston 722) of the piston rod 724 may be connected to a transmission shaft (e.g., the rigid transmission shaft 652, or the flexible transmission shaft 652'). When the piston rod 724 moves towards the front end cap 731 (e.g., move to left as indicated in FIG. 7), the transmission shaft may be actuated to move away from the pneumatic component 700, and further actuate the leaf (e.g., the leaf 612) to move away from the pneumatic component 700. When the piston rod 724 moves towards the rear end cap 732 (e.g., move to right as indicated in FIG. 7), the transmission shaft may be actuated to move towards the pneumatic component 700, and further actuate the leaf (e.g., the leaf 612) to move towards the pneumatic component 700.

It should be noted that the above descriptions of the pneumatic component 700 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, the pneumatic component 700 may also include one or more additional components. For example, the pneumatic component 700 may include a position encoder (not shown in FIG. 7) connected to the piston 722. The position encoder may be capable of moving with the piston 722 to detect the position of the leaf (e.g., the leaf 612).

Figure 8:
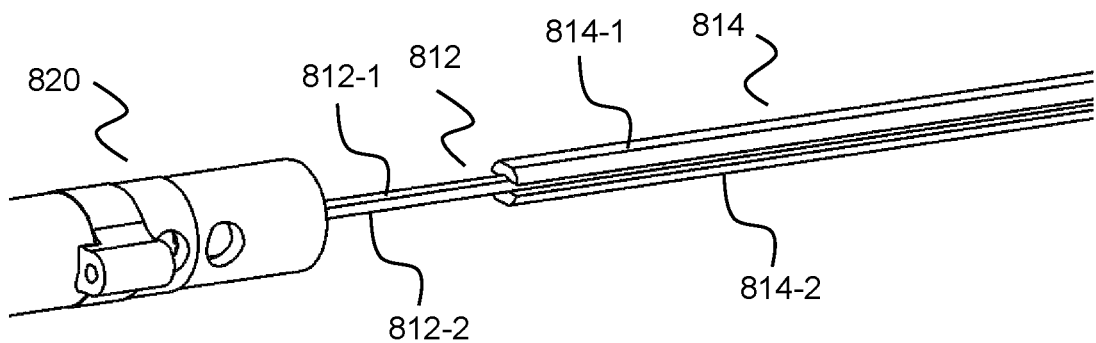
FIG. 8 is a schematic diagram illustrating an exemplary transmission component according to some embodiments of the present disclosure.

FIG. 8 is a schematic diagram illustrating an exemplary transmission component according to some embodiments of the present disclosure. In some embodiments, the transmission component 810 may be a variant of the transmission component 640 as illustrated in FIGS. 6A and 6B. The transmission component 810 may include a modified lead screw 812 and a modified nut 814. The modified lead screw 812 may be connected to a motor drive component 820, such as a shaft of the motor drive component 820. The modified nut 814 may be fixed to a leaf (e.g., the leaf 612). The modified lead screw 812 may be generated by removing a portion of a lead screw on the outer circumference of the lead screw. The modified nut 814 may be generated by removing a portion of a nut.

As shown in FIG. 8, the modified lead screw 812 may include a first surface 812-1 and a second surface 812-2. The first surface 812-1 and the second surface 812-2 may correspond to surfaces on which the portion of the lead screw is removed. The first surface 812-1 and/or the second surface 812-2 may not have external threads. The first surface 812-1 and/or the second surface 812-2 may be flat surface(s) or cambered surface(s). The modified nut 814 may be divided into a first part 814-1 and a second part 814-2. A gap may exist between the first part 814-1 and the second part 814-2. The first part 814-1 and/or the second part 814-2 may include internal threads.

In some embodiments, the modified nut 814 may be connected to the leaf (e.g., the leaf 612) via the external surface of the first part 814-1 and/or the second part 814-2. There may be no relative movement between the modified nut 814 and the leaf (e.g., the leaf 612). In some embodiments, the connection ways may include bonding, inlay, welding, riveting, or the like, or any combination thereof. In some embodiments, the leaf (e.g., the leaf 612) may include six surfaces. A surface forming a radiation field may be referred to as an end surface, and the other surfaces may be referred to as side surfaces. The modified nut 814 may be fixed to any one of the five side surfaces of the leaf (e.g., the leaf 612).

A thickness of the modified lead screw 812 between the first surface 812-1 and the second surface 812-2 may be less than a width of the gap between the first part 814-1 and the second part 814-2. The first surface 812-1 and/or the second surface 812-2 cannot be engaged with the modified nut 814 (e.g., the first part 814-1 and/or the second part 814-2). The modified lead screw 812 may also include a third surface and a fourth surface. The third surface and/or the fourth surface may have external threads. The external threads of the third surface and/or the fourth surface may be engaged with the internal threads of the first part 814-1 and/or the second part 814-2 of the modified nut 814 to actuate the leaf to move when the modified lead screw 812 rotates. For example, when a motor of the motor drive component 820 rotates, the modified lead screw 812 may rotate accordingly. The leaf (e.g., the leaf 612) may be actuated to move linearly by the engagement of the modified lead screw 812 and the modified nut 814. More description of the separation and/or engagement of the modified lead screw 812 and the modified nut 814 may be found elsewhere in the present disclosure (e.g., FIGS. 9A and 9B and the descriptions thereof).

It should be noted that the above descriptions of the transmission component 810 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, the modified nut 814 may be omitted, and the internal threads may be disposed on the leaf (e.g., the leaf 612) directly.

Figure 9A:
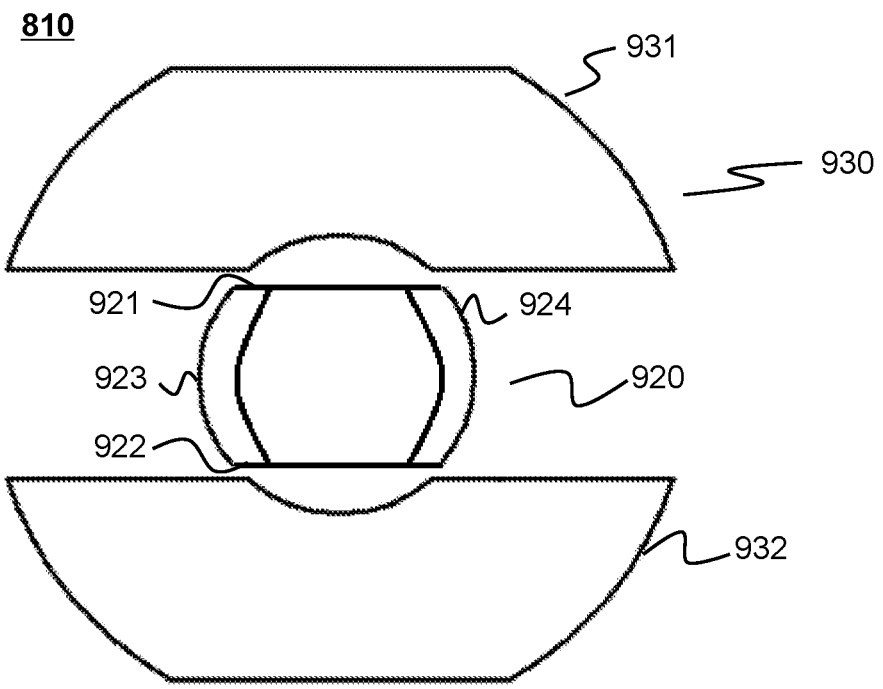
FIGS. 9A and 9B shows two exemplary section views of a transmission component according to some embodiments of the present disclosure.
Figure 9B:
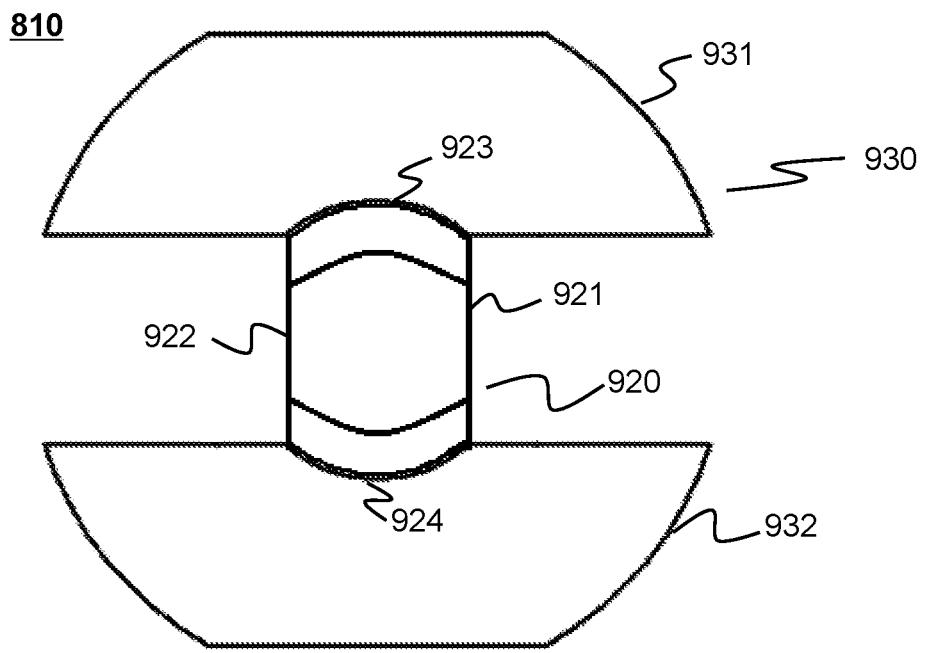

FIGS. 9A and 9B shows two exemplary section views of the transmission component 810 according to some embodiments of the present disclosure. As shown in FIGS. 9A and 9B, the transmission component 810 may include a modified lead screw 920 and a modified nut 930.

The modified lead screw 920 may include a first surface 921, a second surface 922, a third surface 923, and fourth surface 924. The first surface 921 and the second surface 922 may correspond to surfaces on which the portion of the lead screw is removed. In some embodiments, at least a portion of an outer circumference of the modified lead screw may include external threads. For example, the first surface 921 and/or the second surface 922 may not have external threads, while the third surface 923 and/or the fourth surface 924 may have external threads. In some embodiments, a portion of the third surface 923 and/or the fourth surface 924 may have external threads, and the remaining portion of the third surface 923 and/or the fourth surface 924 may not have external threads. The first surface 921 and the second surface 922 may be disposed oppositely, and the third surface 923 and the fourth surface 924 may be disposed oppositely. In some embodiments, the first surface 921 and the second surface 922 may be or may not be parallel to each other. In some embodiments, the first surface 921 and the second surface 922 may be flat surfaces or cambered surfaces. In some embodiments, the modified nut 930 may include a first part 931 and a second part 932. A portion of the modified nut 930 may include a gap. Specifically, the gap may exist between the first part 931 and the second part 932. In some embodiments, the modified lead screw 920 may rotate under the action of a motor of a motor drive component (e.g., the motor 622 of the motor drive component 620). In some embodiments, the rotation (e.g., the angular displacement) of the modified lead screw 920 may be detected by a position encoder of the motor drive component (e.g., the second position encoder 626 of the motor drive component 620) so as to control the engagement and/or separation of the modified lead screw 920 and the modified nut 930.

Merely by way of example, FIG. 9A shows an exemplary first configuration of the modified lead screw 920 and the modified nut 930. When the modified lead screw 920 rotates to the first configuration, the modified lead screw 920 and the modified nut 930 may be in the separation status. As shown in FIG. 9A, the first surface 921 and the second surface 922 may be parallel to the gap of the modified nut 930. The thickness of the modified lead screw 920 between the first surface 921 and the second surface 922 may be less than a width of the gap between the first part 931 and the second part 932 of the modified nut 930. Thus, the modified lead screw 920 and the modified nut 930 may be not engageable with each other. Under this condition, the motor drive component (e.g., the motor drive component 620) cannot actuate the leaf (e.g., the leaf 612) to move. Thus, the leaf (e.g., the leaf 612) may be actuated by the pneumatic component (e.g., the pneumatic component 630, the pneumatic component 700) independently. That is, the modified lead screw 920 may not be engageable with the modified nut 930 when the pneumatic component (e.g., the pneumatic component 630, the pneumatic component 700) actuates the leaf (e.g., the leaf 612) to move. FIG. 9B shows an exemplary second configuration of the modified lead screw 920 and the modified nut 930. When the modified lead screw 920 rotates to the second configuration, the modified lead screw 920 and the modified nut 930 may be in the engagement status. As shown in FIG. 9B, the third surface 923 may be engaged with the first part 931 of the modified nut 930, and the fourth surface 924 may be engaged with the second part 932 of the modified nut 930. When a motor of the motor drive component (e.g., the motor 622 of the motor drive component 620) rotates, the modified lead screw 920 may rotate accordingly. The leaf (e.g., the leaf 612) may be actuated to move linearly by the engagement of the modified lead screw 920 and the modified nut 930. That is, the modified lead screw 920 may be engageable with the modified nut 930 when the motor drive component (e.g., the motor drive component 620) actuates the leaf (e.g., the leaf 612) to move. The modified lead screw 920 and the modified nut 930 may keep engageable when the motor rotates, and thus, the leaf (e.g., the leaf 612) may be actuated to move continuously.

It should be noted that the above descriptions of the transmission component 810 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, in the radiotherapy field, a user may generally concern about the moving speed of a MLC projected in an isocenter plane. The moving speed may be determined based on the actual moving speed of the MLC. The isocenter plane may be a plane passing through an isocenter that is the rotation center of the radiation delivery device 110. In some embodiments, the pneumatic component 630 and the motor drive component 620 may simultaneously actuate a leaf (e.g., the leaf 612) to move to improve the moving speed of the leaf (e.g., the leaf 612). Alternatively or additionally, the pneumatic component 630 may first actuate the leaf (e.g., the leaf 612) to move to a first position at a first speed, and the motor drive component 620 may actuate the leaf (e.g., the leaf 612) to move from the first position to a target position at a second speed. The second speed may be lower than the first speed.

Figure 10:
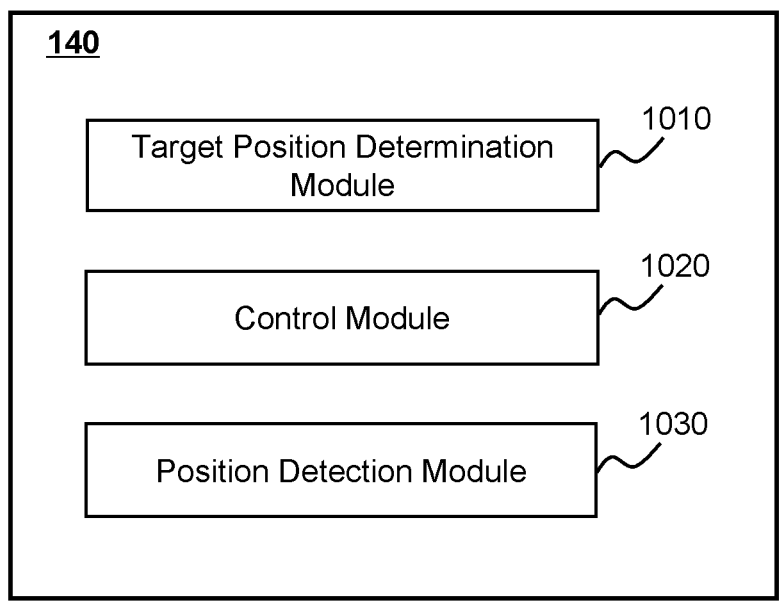
FIG. 10 is a schematic diagram illustrating an exemplary processing device according to some embodiments of the present disclosure.

FIG. 10 is a schematic diagram illustrating an exemplary processing device according to some embodiments of the present disclosure. The processing device 140 may be implemented on the computing device 200 (e.g., the processor 210) as illustrated in FIG. 2 or the CPU 340 as illustrated in FIG. 3. The processing device 140 may include a target position determination module 1010, a control module 1020, and a position detection module 1030.

The target position determination module 1010 may be configured to determine a target position that each of one or more leaves of an MLC needs to reach. In some embodiments, the target position of each leaf may be determined according to a desired radiation field formed by the MLC. In some embodiments, the desired radiation filed may be determined by a radiation treatment plan. The target position determination module 1010 may obtain and/or analyze the radiation treatment plan to determine the shape of the desired radiation field. The target position determination module 1010 may further determine the target position and/or displacement for each of the one or more leaves of the MLC.

The control module 1020 may be configured to control one or more pneumatic components and/or one or more motor drive components. In some embodiments, the control module 1020 may start or close a pneumatic component. The control module 1020 may further control the driving power of the pneumatic component. Alternatively or additionally, the control module 1020 may start or close a motor drive component. The control module 1020 may further control the driving power of the motor drive component or the revolution speed of a motor of the motor drive component. In some embodiments, the control module 1020 may simultaneously control the pneumatic component and the motor drive component to actuate the leaf to move to a target position. Alternatively or additionally, the control module 1020 may non-simultaneously control the pneumatic component and the motor drive component to actuate the leaf to move. For example, the control module 1020 may first control the pneumatic component to actuate the leaf to move to a first position at a first speed, and control the motor drive component to actuate the leaf to move from the first position to a target position at a second speed.

The position detection module 1030 may be configured to detect a position of a leaf. In some embodiments, the position detection module 1030 may be connected to the position detection component including the magnetic grid 616 and the magnetic head 618, the first position encoder of the pneumatic component 630, the second position encoder 626 of the motor drive component 620, or the like, or any combination thereof. The position detection module 1030 may detect the position of the leaf in real-time. For example, the position detection module 1030 may detect the displacement of the leaf and further determine the current position of the leaf based on the displacement of the leaf and an original position.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, any one of the modules may be divided into two or more units. For example, the control module 1020 may be divided into a pneumatic control unit and a motor control unit. The pneumatic control unit may be configured to control one or more pneumatic components, and the motor control unit may be configured to control one or more motor drive components. In some embodiments, the processing device 140 may include one or more additional modules. For example, the processing device 140 may include a storage module (not shown). The storage module may be configured to store data generated during any process performed by any component of the processing device 140.

Figure 11:
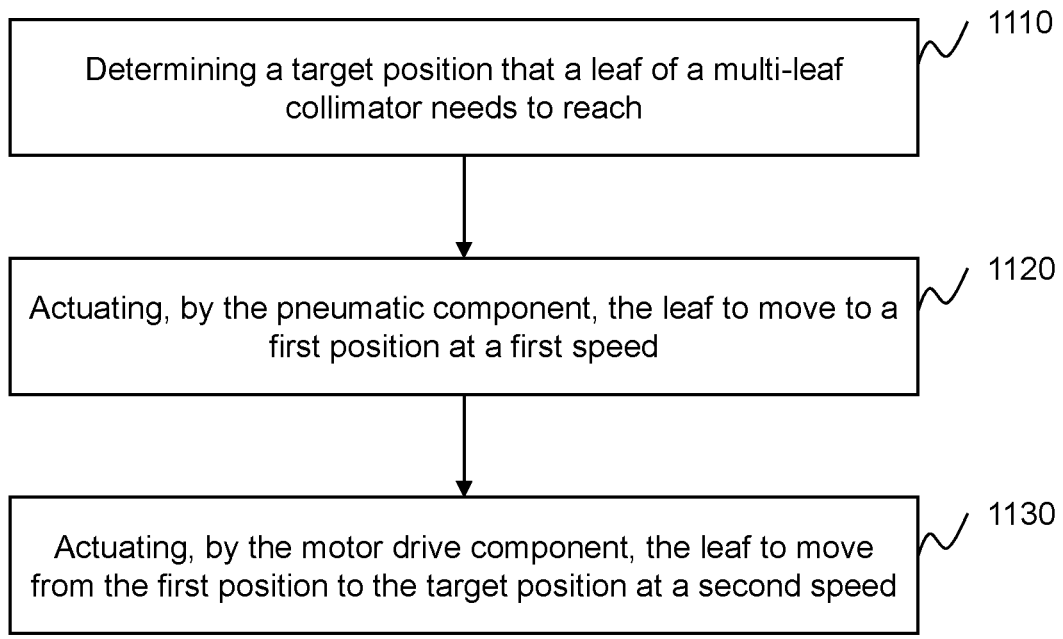
FIG. 11 is a flowchart illustrating an exemplary process for actuating a leaf to move to a target position according to some embodiments of the present disclosure.

FIG. 11 is a flowchart illustrating an exemplary process for actuating a leaf to move to a target position according to some embodiments of the present disclosure. The process 1100 may be implemented in the radiation system 100 illustrated in FIG. 1. For example, the process 1100 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 10). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 140 (e.g., the target position determination module 1010) may determine a target position that a leaf (e.g., the leaf 612) of a MLC needs to reach. In some embodiments, the target position may be determined according to a desired radiation field formed by the MLC. In some embodiments, the target position may refer to a position that the leaf is in a closed state. For example, according to the desired radiation field, the leaf should be moved from an open position to a closed position. Alternatively or additionally, the target position may refer to a position that the leaf is in an open state. For example, according to the desired radiation filed, the leaf should be moved from a closed position to an open position. As another example, according to the desired radiation field, the leaf should be moved from a first open position to a second open position.

In some embodiments, a pneumatic component may provide a larger driving power (or driving force) for the leaf than a motor drive component. The pneumatic component cannot precisely control the displacement of the leaf, while the motor drive component can precisely control the displacement of the leaf. Thus, the pneumatic component may implement the quick movement of the leaf, and the motor drive component may implement the precise movement of the leaf. Specifically, the control module 1020 may first control the pneumatic component to actuate the leaf to move to a first position near the target position, and then control the motor drive component to actuate the leaf to move from the first position to the target position. In some embodiments, the displacement of the leaf may be detected by the position detection module 1030, which is connected to a position detection component including a magnetic grid and a magnetic head (e.g., including the magnetic grid 616 and the magnetic head 618).

In 1120, the processing device 140 (e.g., the control module 1020) may control a pneumatic component (e.g., the pneumatic component 630, the pneumatic component 700) to actuate the leaf (e.g., the leaf 612) to move to a first position at a first speed. To implement the non-simultaneous actuation of the pneumatic component and the motor drive component, the transmission component of the motor drive component may be the transmission component 810 as illustrated in FIG. 8. The transmission component 810 may include a modified lead screw (e.g., the modified lead screw 812, the modified lead screw 920) and a modified nut (e.g., the modified nut 812, the modified nut 930).

Before controlling the pneumatic component to actuate the leaf to move, the modified lead screw and the modified nut should be adjusted to the separation status (e.g., the first configuration illustrated in FIG. 9A). In some embodiments, according to position information detected by a position encoder (e.g., the second position encoder 626), the modified lead screw may rotate with the motor of the motor drive component at a certain angle to ensure that the modified lead screw and the modified nut do not engage with each other. Then the control module 1020 may control the pneumatic component to actuate the leaf to move at the first speed until reaching the first position. In some embodiments, the position detection module 1030 may detect the position of the leaf in real-time. When the leaf reaches the first position, the position detection module 1030 may send a first instruction to the control module 1020. The control module 1020 may stop controlling the pneumatic component to actuate the leaf to move in response to the first instruction.

In 1130, the processing device 140 (e.g., the control module 1020) may control a motor drive component (e.g., the motor drive component 620) to actuate the leaf to move from the first position to the target position at a second speed. The second speed may be lower than the first speed.

In some embodiments, before controlling the motor drive component to actuate the leaf to move, the modified lead screw and the modified nut should be adjusted to the engagement status (e.g., the first configuration illustrated in FIG. 9B). In some embodiments, according to position information detected by a position encoder (e.g., the second position encoder 626), the modified lead screw may rotate with the motor of the motor drive component at a certain angle to ensure that the modified lead screw and the modified nut engage with each other. Then, the control module 1020 may control the motor drive component to actuate the leaf to move at the second speed until the leaf reaches the target position. In some embodiments, the position detection module 1030 may detect the position of the leaf in real-time. When the leaf reaches the target position, the position detection module 1030 may send a second instruction to the control module 1020. The control module 1020 may stop controlling the motor drive component to actuate the leaf to move in response to the second instruction.

In the embodiments of the present disclosure, the pneumatic component may actuate the leaf to move to a first position at a first speed when the modified lead screw is not engageable with the modified nut. The motor drive component may actuate the leaf to move from the first position to the target position at a second speed when the modified lead screw is engageable with the modified nut. Therefore, the quick movement and the precise movement of the leaf may be achieved by the non-simultaneous actuation of the pneumatic component and the motor drive component.

It should be noted that the above description of the process 1100 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, whether the modified lead screw is engaging with the modified nut may be determined according to the detected current of the motor. Specifically, if the detected current of the motor is less than or equal to a first current threshold, it may be determined that the modified lead screw and the modified nut are in the separation status. If the detected current of the motor is greater than the first current threshold and less than or equal to the second current threshold, it may be determined that the modified lead screw and the modified nut are in the engagement status. In some embodiments, each leaf of the MLC may be move to the target position according to process 1100, and thus, the desired radiation field may be formed.

Figure 12:
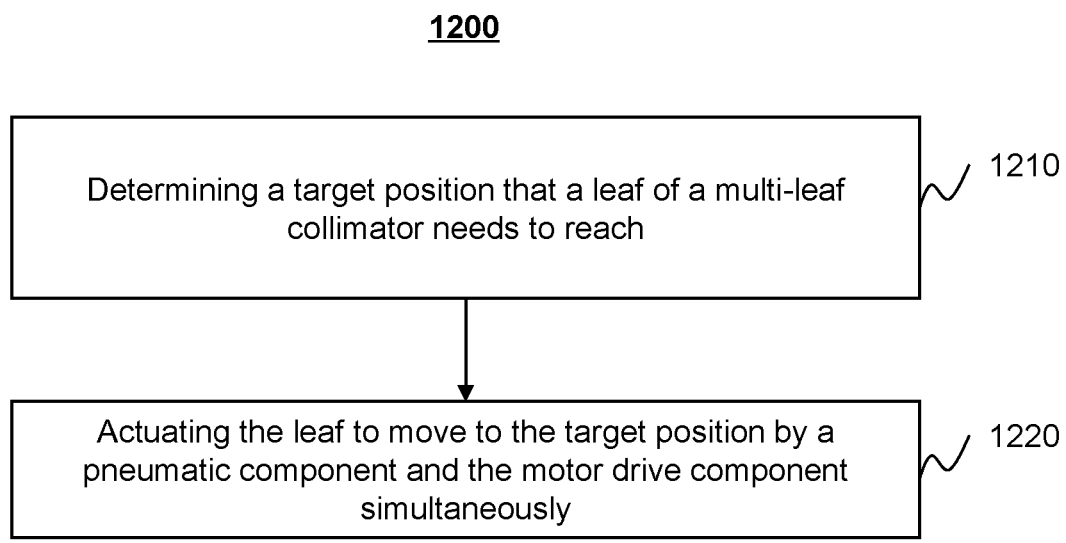
FIG. 12 is a flowchart illustrating an exemplary process for actuating a leaf to move to a target position according to some embodiments of the present disclosure.

FIG. 12 is a flowchart illustrating an exemplary process for actuating a leaf to move to a target position according to some embodiments of the present disclosure. The process 1200 may be implemented in the radiation system 100 illustrated in FIG. 1. For example, the process 1200 may be stored in the storage device 150 and/or the storage 220 in the form of instructions (e.g., an application), and invoked and/or executed by the processing device 140 (e.g., the processor 210 illustrated in FIG. 2, the CPU 340 as illustrated in FIG. 3, or one or more modules in the processing device 140 illustrated in FIG. 10). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1210, the processing device 140 (e.g., the target position determination module 1010) may determine a target position that a leaf of a MLC (e.g., the leaf 612) needs to reach. In some embodiments, the target position may be determined according to a desired radiation field formed by the MLC. In some embodiments, the target position may refer to a position that the leaf is in a closed state. For example, according to the desired radiation field, the leaf should be moved from an open position to a closed position. Alternatively or additionally, the target position may refer to a position that the leaf is in an open state. For example, according to the desired radiation filed, the leaf should be moved from a closed position to an open position. As another example, according to the desired radiation field, the leaf should be moved from a first open position to a second open position.

In 1220, the processing device 140 (e.g., the control module 1020) may control a pneumatic component (e.g., the pneumatic component 630, the pneumatic component 700) and a motor drive component (e.g., the motor drive component 620) to simultaneously actuate the leaf to move to the target position. Since the pneumatic component and the motor drive component actuate the leaf simultaneously, the pneumatic component and the motor drive component may actuate the leaf to move at the same speed. In some embodiments, the position detection module 1030 may detect the position of the leaf in real-time. When the leaf reaches the target position, the position detection module 1030 may send a third instruction to the control module 1020. The control module 1020 may stop controlling the pneumatic component and the motor drive component to actuate the leaf to move in response to the third instruction.

In some embodiments, the transmission component of the motor drive component may be the transmission component 640 as illustrated in FIG. 6. The transmission component 640 may include a lead screw and a nut that are engageable with each other. Alternatively or additionally, the transmission component of the motor drive component may be the transmission component 810 as illustrated in FIG. 8. The transmission component 810 may include a modified lead screw and a modified nut. The modified lead screw and the modified nut may be kept in the engagement status.

In the embodiments of the present disclosure, the leaf may be actuated to move by the pneumatic component and the motor drive component simultaneously, which may improve the moving speed of the leaf without increasing the driving power of the motor drive component.

It should be noted that the above description of the process 1200 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the leaf may be actuated by the motor drive component only.

In the present disclosure, the pneumatic component and the motor drive component may jointly actuate the leaf to move, which may improve the moving speed of the leaf (e.g., from 25 mm/s to 250 mm/s). A flexible transmission shaft may be used to connect the pneumatic component and the leaf, and thus the pneumatic component may be arranged flexibly. What's more, a modified transmission component (including a modified lead screw and a modified nut) may be used to connect the motor drive component and the leaf. When the modified lead screw and the modified nut are in the separation status, the leaf may be actuated by the pneumatic component only. When the modified lead screw and the modified nut are in the engagement status, the leaf may be actuated by the motor drive component, or by the motor drive component and the pneumatic component simultaneously.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A multi-leaf collimator, comprising:
  a plurality of leaf modules;
  wherein each leaf module of the plurality of leaf modules includes:
    a leaf configured to shield a portion of beams emitted by a radiation source, the leaf being movable along a guide rail of the multi-leaf collimator; and
    a drive mechanism including a first drive component and a second drive component, the first drive component and the second drive component being both connected to the leaf, wherein the first drive component and the second drive component jointly actuate the leaf to move along the guide rail.

2. The multi-leaf collimator of claim 1, wherein the second drive component includes:
  an air cylinder configured to accommodate compressed gas;
  a piston configured to output a driving force to the leaf when driven by the compressed gas, the piston being connected to the air cylinder; and
  a first position encoder connected to the piston, the first position encoder being capable of moving with the piston to detect a position of the leaf.

3. The multi-leaf collimator of claim 2, further comprising:
  a transmission shaft configured to transmit the driving force to the leaf, wherein a first end of the transmission shaft is connected to the piston, and a second end of the transmission shaft is connected to the leaf.

4. The multi-leaf collimator of claim 3, wherein the transmission shaft is flexible and is configured to arrange the air cylinder flexibly, and each leaf module of the plurality of leaf modules further includes:
  a shaft sleeve configured to accommodate the flexible transmission shaft.

5. The multi-leaf collimator of claim 1, wherein the first drive component includes a speed increaser configured to increase a revolution speed of the first drive component.

6. The multi-leaf collimator of claim 1, further comprising:
  a transmission component coupled to the first drive component, the transmission component being configured to transmit a driving force to the leaf.

7. The multi-leaf collimator of claim 6, wherein the transmission component includes:
  a lead screw connected to the first drive component and rotatable with a rotation of a motor of the first drive component; and
  a nut fixed to the leaf, wherein
    the lead screw further includes a plurality of external threads, the nut further includes a plurality of internal threads, and the plurality of internal threads of the nut are engageable with the external threads of the lead screw for actuating the leaf to move when the lead screw rotates.

8. The multi-leaf collimator of claim 1, wherein the first drive component and the second drive component simultaneously actuate the leaf to move along the guide rail, wherein the first drive component and the second drive component actuate the leaf to move with a same speed.

9. The multi-leaf collimator of claim 1, wherein the first drive component and the second drive component non-simultaneously actuate the leaf to move along the guide rail.

10. The multi-leaf collimator of claim 9, wherein the second drive component firstly actuates the leaf to move to a first position at a first speed, and the first drive component actuates the leaf to move from the first position to a target position at a second speed, the second speed being lower than the first speed.

11. The multi-leaf collimator of claim 10, further comprising:
  a transmission component including a modified lead screw and a modified nut, wherein the modified lead screw is connected to the first drive component, and the modified nut is fixed to the leaf.

12. The multi-leaf collimator of claim 11, wherein at least a portion of an outer circumference of the modified lead screw includes external threads.

13. The multi-leaf collimator of claim 11, wherein the modified lead screw includes a first surface and a second surface, and a portion of the modified nut includes a gap, wherein a thickness of the modified lead screw between the first surface and the second surface is less than a width of the gap of the portion of the modified unit.

14. The multi-leaf collimator of claim 13, wherein
  the modified lead screw is not engageable with the modified nut when the second drive component actuates the leaf to move, or
  the modified lead screw is engageable with the modified nut when the first drive component actuates the leaf to move.

15. A system for controlling a multi-leaf collimator, comprising:
  at least one storage device including a set of instructions for controlling a movement of the multi-leaf collimator;
  at least one processor in communication with the at least one storage device, wherein when executing the set of instructions, the at least one processor is configured to cause the system to:
    determine a target position that a leaf of the multi-leaf collimator needs to reach; and
    actuate, by a first drive component and a second drive component, the leaf to move to the target position, wherein the first drive component and the second drive component are both connected to the leaf, and each drive component independently actuates the leaf.

16. The system of claim 15, wherein to actuate the leaf to move to the target position, the at least one processor is further configured to cause the system to:
  actuate the leaf to move to the target position by the first drive component and the second drive component simultaneously.

17. The system of claim 15, wherein to actuate the leaf to move to the target position, the at least one processor is further configured to cause the system to:
- actuate, by the second drive component, the leaf to move to a first position at a first speed; and
- actuate, by the first drive component, the leaf to move from the first position to the target position at a second speed, the second speed being lower than the first speed.

18. The system of claim 15, wherein the multi-leaf collimator includes a transmission component including a modified lead screw and a modified nut, wherein the modified lead screw is connected to the first drive component, and the modified nut is fixed to the leaf.

19. The system of claim 18, wherein the at least one processor is further configured to cause the system to:
- determine whether the modified lead screw is engaging with the modified nut;
- in response to a determination that the modified lead screw is not engageable with the modified nut, actuate the leaf to move to a first position by the second drive component; and
- actuate the leaf to move from the first position to the target position by the first drive component.

20. The system of claim 19, wherein the at least one processor is further configured to cause the system to:
- in response to a determination that the modified lead screw is engageable with the modified nut, adjust the modified lead screw such that the modified lead screw is not engageable with the modified nut;
- actuate the leaf to move to the first position by the second drive component; and
- actuate the leaf to move from the first position to the target position by the first drive component.

21. A method implemented on a computing device having at least storage device and at least one processor, comprising:
- determining a target position that a leaf of a multi-leaf collimator needs to reach; and
- actuating, by a first drive component and a second drive component, the leaf to move to the target position, wherein the first drive component and the second drive component are both connected to the leaf, and each drive component independently actuates the leaf.

* * * * *